June 27, 1944. W. E. LAMMERTS Plant Pat. 632
ROSE PLANT
Filed Jan. 4, 1944
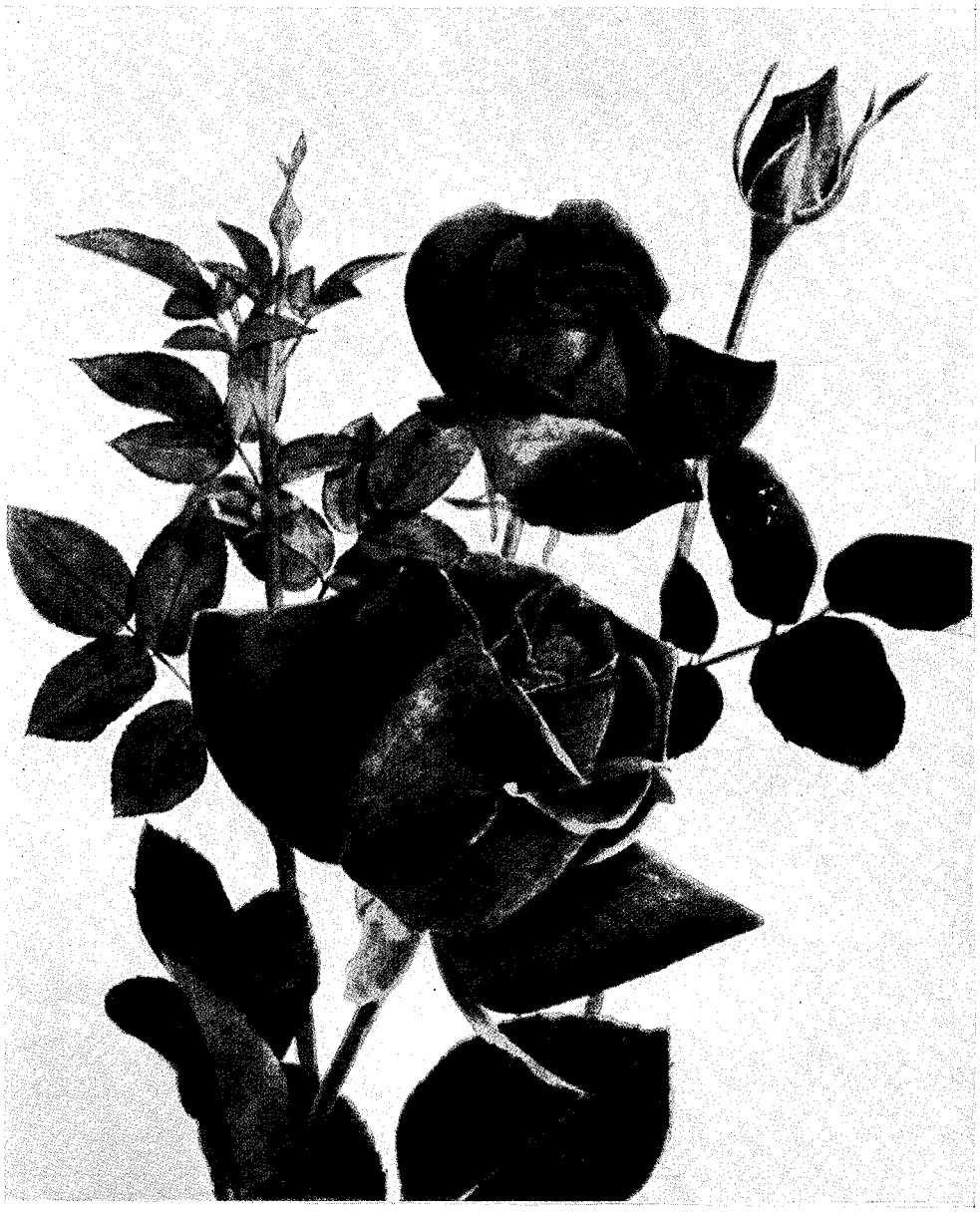
Inventor
Walter E. Lammerts
By Robb & Robb
attorneys Patented June 27, 1944

Plant Pat. 632

UNITED STATES PATENT OFFICE

632

ROSE PLANT

Walter E. Lammerts, West Los Angeles, Calif., assignor to Armstrong Nurseries, Inc., Ontario, Calif., a corporation of California Application January 4, 1944, Serial No. 516,957

1 Claim. (Cl. 47—61)

The present invention relates to a new and distinct variety of Rose plant, resulting from the growing of seed from a cross of the two varieties "Night" and "Charlotte Armstrong."

It will be noted as this description proceeds that the novelty of this new variety arises from the fact that it embodies a combination of many of the valuable characteristics of its two parents, and therefore represents a very desirable improvement in hybrid teas.

Particularizing with reference to the above, its growth habit, the color of flower and the fragrance thereof are similar to those of its parent "Night," whereas in vigor, flower shape and petalage, it resembles more its parent "Charlotte Armstrong." Specifically, this new rose has between forty and forty-five petals, whereas "Night" has between sixteen and twenty-five, and "Charlotte Armstrong" approximately thirty-five petals. It is much more resistant to mildew and blackspot than its seed parent, but is not quite as resistant as its pollen parent, and in the cool Pacific Coast sections has about the same susceptibility to rust as its parent "Night."

Referring now to the bud, that of this new rose is intermediate in length and form of those characteristics in the parents, being much longer and larger in size than the bud of "Night" and equal to that of "Charlotte Armstrong" in overall size, but not as long as in this latter variety.

Comparing the foliage of the new rose with that of its parents, it has the shape of the variety "Night," but the texture is more like that of "Charlotte Armstrong."

This variety is at its best in the hot interior climates, but is equally as satisfactory in the coastal climates where it is not allowed to become infested with rust.

The flowers are distinctive because they characteristically contain two tones of red when the flower is newly opened, the central portion being somewhat lighter in color than that of the outer portion. The fading reaction differs from most red roses in that in this one the old flowers are what are popularly called violet in color, whereas most red roses fade to a bluish-pink.

Continuing the comparison with other leading red roses, it is to be noted that this new rose is more upright, more mildew resistant (as determined by observations made with respect to those grown under comparable conditions), deeper in color and more vigorous than "Crimson Glory" and has spicier fragrance. It is more prolific, more symmetrical, upright and deeper in color than "Etoile de Hollande," but not as mildew resistant as that variety. It has a better coverage of foliage, a greater depth and intensity of color than "Heart's Desire," but does not have as long a bud as "Heart's Desire."

Asexual reproduction of this new variety shows the foregoing characteristics come true to form and are established.

The distinctiveness and novelty of this new variety may be readily recognized from the foregoing comparative summary, and are more particularly pointed out in the following detailed description in which color terminology accords with that of the Robert F. Wilson Horticultural Colour Chart:

Type: Half hardy; bush; outdoor; seedling; for cut flowers and garden decoration.

Class: Hybrid tea.

Breeding or discovery: Seedling.

*Seed parent.*—"Night."

*Pollen parent.*—"Charlotte Armstrong."

Propagation: Holds its distinguishing characteristics through succeeding propagations by budding, which is the only method tried up to the present.

*Flower*

Locality where grown: Ontario, California.

Flowers borne: Singly, two, three, four to stem; in irregular, flat cluster; on strong, medium to long stems.

Quantity of bloom: Free; outdoors.

Continuity: Nearly continuous in mild climate.

Fragrance: Strong; tea and spicy.

Bud:

*Pedicel.*—Medium length; medium to heavy; erect; almost smooth; numerous gland-tipped cilia. *Color*—Fern Green—o862/2—Chart II, page 186, blotched with Pansy Purple—928/3—Chart II, page 177.

*Before calyx breaks.*—*Size*—large.—*Form*—short, pointed, ovoid, with foliaceous appendages on the surface of the bud; with much cut, bristle-like foliaceous parts extending beyond the tip of the bud equal to one-half of its length. *Color*—Oxblood Red—oo823—Chart II, page 191.

*As calyx breaks.*—*Color*—Indian Lake—826—Chart II, page 170. *Inner surface*—with woolly tomentum. *Margins*—margins of alternate sepals and alternate margins lined with bland-tipped cilia.

*As first petal opens.*—*Size*—large. *Form*—Ovoid and globular. *Color*—outside—Chrysanthemum Crimson—824—Chart II, page 169, to Indian Lake—826—Chart II, page 170. Inside—Ruby Red—827—Chart II, page 171, to Chrysanthemum Crimson—824—Chart II, page 169. *Opening*—opens up well. It is retarded from opening by cold and wet weather.

Bloom:

*Size.*—When fully open, large; five inches to six inches.

*Petalage.*—Very double (many petals, usually with no stamens showing), from 40 to 45 petals; arranged irregularly.

*Form.*—Globular at first; becoming cupped to globular; petals remaining at first moderately tightly cupped but rolled outward; becoming later, at maturity, tightly rolled outward.

Petals: Thick; leathery; with inside velvety and outside satiny.

*Shape.*—Outside—round. Intermediate—round, with apex curled out and slightly creped. Inside—obovate, with apex flat.

This description of a newly opened flower was made from a rose grown outdoors, in October, 1942, at Ontario, California:

*Color.*—Outside petal: Outside surface—Chrysanthemum Crimson—824/3—Chart II, page 169, to Tyrian Rose—24—Chart I, page 24. Inside surface—Cardinal Red—822/2—Chart II, page 168. Intermediate petal: Outside surface—Tyrian Rose—24—Chart I, page 24. Inside surface—Rose Red—724/1—Chart II, page 158. Inner petal: Outside surface—Rose Red—724—Chart II, page 158. Inside surface—Chrysanthemum Crimson—824/3—Chart II, page 169, to Rose Red—724—Chart II, page 158. Base of outside, intermediate, and inner petals, Primrose Yellow—6o1/1—Chart I, page 65, and confined to tip of base.

This description was made from a rose that was open for three days outdoors, in October, 1942, at Ontario, California:

*Color.*—Outside petal: Outside surface—Rose Red—724/2—Chart II, page 158. Inside surface—Indian Lake—826/3—Chart II, page 170, to Tyrian Purple—727—Chart II, page 159. Inside petal: Outside surface—Tyrian Rose—24/1—Chart I, page 24. Inside surface—Tyrian Rose—24—Chart I, page 24. Base of outside and inside petals, Primrose Yellow—6o1/1—Chart I, page 65, and confined only to tip of base.

*General color effect.*—Newly opened flower—Chrysanthemum Crimson—824/1—Chart II, page 169. Three days open—Tyrian Purple—727—Chart II, page 159.

*Behavior.*—Drop off cleanly; affected by cold and wet weather; fading from chrysanthemum Crimson—824/1—Chart II, page 169, to Tyrian Purple—727/2—Chart II, page 159.

*Flower longevity.*—On bush in garden five days in October; cut roses grown outdoors kept at living-room temperatures, five days in October.

*Reproduction organs*

Stamens: Medium number; arranged regularly about pistils, mixed with petaloids and tucked in calyx.

Filaments: Medium long; some Rhodonite Red—oo22/2—Chart II, page 188; others Chrome Yellow—6o5/3—Chart II—page 154. Most with anthers.

Anthers: Medium size; open at various times; Chrome Yellow—6o5/2—Chart II, page 144.

Pollen: Moderate.

*Color.*—Nasturtium Orange—610—Chart II, page 145.

Pistils: Medium number; very hairy.

Styles: Uneven; medium length; medium heavy; bunched; very hairy. Tips, Cardinal Red—822/2—Chart II, page 168. Base, Sap Green—62/1—Chart I, page 62.

Stigma: Amber Yellow—5o5/2—Chart II, page 132.

Ovaries: Enclosed in calyx with some protruding therefrom.

Hips: Short; globular, with inconspicuous neck; Lettuce Green—861/1—Chart II, page 176, before maturity; very smooth; walls thick; fleshy.

Sepals: Permanent; long; spear-shaped; recurved.

*Color.*—Inside—Lavender Green—ooo761—Chart II, page 196. Outside—Lettuce Green—861/1—Chart II, page 176.

Seeds: Few; large.

*Plant*

Foliage:

*Leaves.*—Compound of three, five and seven leaflets; normal in amount; large; leathery; semi-glossy.

*Leaflets.*—Shape—oval, with apex mucronate. Base—round. Margin—simply serrate.

*Color.*—*Mature*—upper surface—Parsley Green—oo962/1—Chart II, page 193. Under surface—Lavender Green—ooo761—Chart II, page 196. *Young*—upper surface—Sage Green—ooo861—Chart II, page 198. Under surface—Willow Green—ooo862—Chart II, page 199, slightly washed with Garnet Brown—ooo918/3—Chart II, page 192.

*Rachis (the supporting stem of the compound leaf).*—Medium heavy. Upper side—grooved; hairy and glandular. Under side—smooth; hairy and glandular.

*Stipules.*—Short; medium width; with medium length points, turning out at an angle of less than 45°, slightly recurved toward the stem.

*Disease.*—Fairly resistant to mildew; susceptible to rust on the Pacific Coast.

Growth:

*Habit.*—Upright; much branched.

*Growth.*—Vigorous.

*Canes.*—Heavy.

*Main stems.*—Spinach Green—o960/3—Chart II, page 187; some cracks in bark usually forming a corky linear line along stem. *Large prickles*—several; medium length; straight; hooked to downward; with long to medium narrow base. Color—Erythrite Red—oo27/1—Chart II, page 190. *Small prickles*—several. Color—Erythrite Red—oo27/1—Chart II, page 190. *Hairs*—few, Color—Erythrite Red—oo27/1—Chart II, page 190.

*Branches.*—*Color*—Spinach Green—o960/3—Chart II, page 187, but shaded near ends with Erythrite Red—oo27/1—Chart II, page 190. *Large prickles*—several; medium to long; straight; hooked to downward; with long, narrow base. *Small prickles*—several to many. Color—Erythrite Red—oo27/1—Chart II, page 190. *Hairs*—several. Color—Erythrite Red—oo27/1—Chart II, page 190.

*New shoots.*—Fern Green—o862/2—Chart II, page 186. *Large prickles*—several; medium to long; straight; hooked to downward; with long, narrow base. Color—Erythrite Red—oo27/1—Chart II, page 190. *Small prickles*—several. Color—Erythrite Red—oo27/1—Chart II, page 190. *Hairs*—several. Color — Erythrite Red—oo27/1—Chart II, page 190.

I claim:

A new and distinct variety of Rose plant characterized as to novelty by its habits of growth, fragrance and two-tone color of the flower and its fading characteristic, very double petalage, shape and size of the buds, shape and texture of the plant foliage, and disease resistance, substantially as shown and described.

WALTER E. LAMMERTS.